United States Patent [19]

Sierra

[11] Patent Number: 6,110,484
[45] Date of Patent: Aug. 29, 2000

[54] COLLAGEN-POLYMER MATRICES WITH DIFFERENTIAL BIODEGRADABILITY

[75] Inventor: David H. Sierra, Atherton, Calif.

[73] Assignee: Cohesion Technologies, Inc., Palo Alto, Calif.

[21] Appl. No.: 09/199,139

[22] Filed: Nov. 24, 1998

Related U.S. Application Data

[62] Continuation of application No. 08/537,896, filed as application No. PCT/US95/12802, Oct. 3, 1995, abandoned, and a continuation-in-part of application No. 08/522,299, filed as application No. PCT/US94/11209, Oct. 3, 1994, abandoned.

[51] Int. Cl.⁷ .............................. A61F 2/00; A61F 2/01; A61F 13/00
[52] U.S. Cl. .................. 424/426; 424/422; 424/423; 424/426; 424/444; 514/774; 530/354
[58] Field of Search .................... 424/422, 423, 424/426, 428, 444; 514/774, 772.2; 530/356, 381, 382, 354

[56] References Cited

U.S. PATENT DOCUMENTS

| | | | |
|---|---|---|---|
| 3,909,852 | 10/1975 | Homsy | 3/1.9 |
| 4,010,494 | 3/1977 | Sauer | 3/1 |
| 4,052,754 | 10/1977 | Homsy | 3/1.9 |
| 4,061,731 | 12/1977 | Gottlieb | 424/101 |
| 4,291,013 | 9/1981 | Wahlig et al. | 424/16 |
| 4,361,510 | 11/1982 | Mitra | 260/112 |
| 4,373,217 | 2/1983 | Draenert | 3/1.9 |
| 4,563,489 | 1/1986 | Urist | 524/21 |
| 4,596,574 | 6/1986 | Urist | 623/16 |
| 4,627,879 | 12/1986 | Rose et al. | 106/124 |
| 4,636,526 | 1/1987 | Dorman et al. | 521/61 |
| 4,661,536 | 4/1987 | Dorman et al. | 523/113 |
| 4,698,375 | 10/1987 | Dorman et al. | 523/115 |
| 4,702,917 | 10/1987 | Schindler | 424/422 |
| 4,714,457 | 12/1987 | Alterbaum | 494/37 |
| 4,722,948 | 2/1988 | Sanderson | 523/115 |
| 4,842,603 | 6/1989 | Draenert | 623/16 |
| 4,843,112 | 6/1989 | Gerhart et al. | 523/113 |
| 4,849,285 | 7/1989 | Dillon | 428/330 |
| 4,859,383 | 8/1989 | Dillon | 264/43 |
| 4,863,974 | 9/1989 | Mallouk et al. | 521/85 |
| 4,898,734 | 2/1990 | Mathiowitz et al. | 424/426 |
| 4,902,295 | 2/1990 | Walthall et al. | 623/11 |
| 4,950,483 | 8/1990 | Ksander et al. | 424/422 |
| 5,024,841 | 6/1991 | Chu et al. | 424/422 |
| 5,032,445 | 7/1991 | Scantlebury et al. | 428/158 |
| 5,077,049 | 12/1991 | Dunn et al. | 424/426 |
| 5,093,179 | 3/1992 | Scantlebury et al. | 428/158 |
| 5,098,779 | 3/1992 | Kranzler et al. | 428/306.6 |
| 5,141,522 | 8/1992 | Landi | 623/66 |
| 5,197,976 | 3/1993 | Herweek et al. | 623/1 |
| 5,290,552 | 3/1994 | Sierra et al. | 424/94.64 |
| 5,292,802 | 3/1994 | Rhee et al. | 525/54.1 |
| 5,354,682 | 10/1994 | Kingdon et al. | 435/214 |
| 5,411,500 | 5/1995 | Herweck et al. | 623/1 |
| 5,411,885 | 5/1995 | Marx | 435/240.2 |
| 5,522,895 | 6/1996 | Mikos | 623/16 |

FOREIGN PATENT DOCUMENTS

| | | |
|---|---|---|
| 0 192 068 | 8/1986 | European Pat. Off. . |
| 0 341007 | 11/1989 | European Pat. Off. . |
| 0 485210 | 5/1992 | European Pat. Off. . |
| 0 539 751 | 5/1993 | European Pat. Off. . |
| 0 560 014 | 9/1993 | European Pat. Off. . |
| WO 90/03768 | 4/1990 | WIPO . |
| WO 91/16063 | 10/1991 | WIPO . |
| WO 92/09301 | 6/1992 | WIPO . |
| WO 92/13565 | 8/1992 | WIPO . |
| WO 93/16739 | 9/1993 | WIPO . |
| WO 94/07432 | 4/1994 | WIPO . |
| WO 94/16085 | 7/1994 | WIPO . |
| WO 94/22503 | 10/1994 | WIPO . |
| WO 95/03011 | 2/1995 | WIPO . |
| WO 95/15763 | 6/1995 | WIPO . |

OTHER PUBLICATIONS

Pandit et al. Abstract #123 presented at the 4th Annual Meeting of Wound Healing Society. May 18–21, 1994.

Doillon et al. Porosity and biological properties of polyethylene–glycol–conjugated collagen materials. vol. 6(8). 715–728, 1994.

Cheung et al., "The effect of γ–irridiation on collagen molecules, isolated α–chains, and crosslinked native fibers", *J. Biomed. Materials Res.* (1990) 24:581–589.

Grant, et al., "The effects of gamma irradiation on the structure and reactivity of native and crosslinked collagen fibres" *J. Anat.* (1973) 115:29–43.

Labout, "Gamma–radiation in collagen solutions influence of solutes on the gelation dose" *Int. J. Radiat. Biol.* (1972) 21:482–492.

Liu et al., "The effect of gamma irradiation on injectable human amnion collagen" *J. Biomed. Materials Res.* (1989) 23:833–844.

Pandit et al., "In vivo response of acidic fibroblast growth factor (FGF–1), delivered through a porous fibrin scaffold on wound healing" *4th Annual Scientific Meeting of the Wound Healing Society* (May 18–21, 1994), Mark Hopkins Hotel, San Francisco, CA (abstract No. 122) 1 page total.

Pandit et al., "In vivo response of a porous fibrin scaffold on wound healing" *4th Annual Scientific Meeting of the Wound Healing Society* (May 18–21, 1994), Mark Hopkins Hotel, San Francisco, CA (abstract No. 123) 1 page total.

Pandit et al., "The effect of a porous degradable fibrin scaffold on wound healing" *The 20th Annual Meeting of the Society for Biomaterials* (Apr. 5–9, 1994), Boston, MA, p. 34.

Ramanathan et al., "The effect of γ–radiation on soluble and insoluble collagens" *Biochim. Biophys. Acta* (1965) 102:533–541.

Sliwowski et al., "Influence of gamma radiation on the solubility of collagen–derived membranes" *Material Medica Polona* (1976) 4:379–381.

Vainio, "Non–metallic fixatives in orthopedic surgery. Some aspect of their present and future properties"*Arch. Orthop. Traumat. Surg.* (1978) 92: 169–174.

*Primary Examiner*—Thurman K. Page
*Assistant Examiner*—Lakshmi Channavajjala
*Attorney, Agent, or Firm*—Morrison & Foerster

[57] ABSTRACT

The current invention is a biomedical implant comprising a biomedical matrix material and a biodegradable porosifying agent. As the porosifying agent degrades in situ, an implant with an inter-connecting network is formed. The resultant mechanically stable implant allows for tissue and fluid influx into the matrix. The invention is also directed to a method for repair of mammalian tissue using the above-described implant.

1 Claim, No Drawings

COLLAGEN-POLYMER MATRICES WITH DIFFERENTIAL BIODEGRADABILITY

CROSS REFERENCE TO RELATED APPLICATIONS

This application is a continuation of U.S. Ser. No. 08/537,896, filed on Oct. 12, 1995, now abandoned, which is a U.S. filing under 35 U.S.C. §371(c) of PCT/US95/12802, filed on Oct. 3, 1995, which published as WO 96/10428 and claims priority to PCT/US94/11209, filed on Oct. 3, 1994, which published as WO 96/10374. U.S. Ser. No. 08/537,896 is also a continuation-in-part of U.S. Ser. No. 08/522,299 filed on Sep. 25, 1995, now abandoned, which is a U.S. filing under 35 U.S.C. §371(c) of PCT/US94/11209.

DESCRIPTION

1. Technical Field

This invention is in the general field of biomaterials. More specifically, the invention is directed to biomedical implants, their composition and methods of preparation and use.

2. Background of the Invention

Biomaterials have been used for implantation into the human body to act as supports for wound and solid tissue healing. Matrices useful for this purpose should have the ability to adhere and conform to the wound site and surrounding tissue. Ideally, they also should facilitate accumulation of fibroblasts, endothelial cells and wound healing regulatory cells to promote connective tissue deposition and angiogenesis.

U.S. Pat. No. 4,849,285 to Dillon is directed to a composite, self-supporting agglomerated microstructure useful as a surgical implant. The macrostructure is a matrix of polytetrafluoroethylene resin and cured silicone that has uniformly distributed within it a particulate material. These particulates have a maximum size of about 2000 microns and may be hydroxyapatite or tricalcium phosphate. This particular macrostructure, therefore, is a composite of ceramic particulate material and organic biomaterials that is uniformly permeated by a network of open pores. The pores are formed by incorporating sodium chloride into the composite and thereafter leaching it out in the manufacturing process.

U.S. Pat. No. 4,843,112 to Gerhart et al. is to a bone cement composed of a particulate biocompatible calcium phosphate ceramic and a resorbable calcium salt disperses in a crosslinked biodegradable polyester matrix. Pores are created in the matrix by body fluids creating small voids or cavities in the polymer matrix.

U.S. Pat. No. 5,141,522 to Landi et al. describes a composite of two or more biocompatible polymers useful for mammalian tissue repair. One of the polymers is polytetrafluoroethylene (PTFE), which is the reinforcing binder. A bioabsorbable component that may be a lactone, carbonate or a lactide, is contained within the structure of the PTFE and serves to enhance ingrowth of tissue.

Additional disclosures of PFTE compositions useful as implants include, but are not limited to U.S. Pat. Nos. 5,141,522; 5,098,779; and 4,863,974. The PFTE component of these compositions serves as a nonabsorbable microfibrillar structural support. A bioabsorbable component is contained or coated on the structural support. The PFTE is polymerized prior to implantation of the compositions.

U.S. Pat. No. 4,373,217 to Draenert is directed to a polymeric implant material that has an acrylate, polymethacrylate or copolymer base with dispersed resorbable tricalcium phosphate of 50 to 300 microns with an available pore volume of less than 0.1 mL/g. This particular material is said to allow for a firm bond between implant and body tissue. Resorption of tricalcium phosphate particles at the surface of the implant are resorbed into the body is said to promote bone growth in the marginal porosity produced. In order to ensure absorption of liquid monomer into the porous calcium phosphate, a filler that is also resorbable in the body is included to fill the pore volumes of the calcium phosphate.

U.S. Pat. No. 4,898,734 to Mathiowitz et al. also involves a precast solid polymeric implant material. A continuous polymeric matrix made of, for example, polyurethane or polystyrene, is embedded with microcapsules or microspheres that may contain material for subsequent release. The spheres may be removed from the matrix by bioerosion. For creation of a vascular graft, erodible microspheres are entrapped within a tube-shaped slower-degrading polymer matrix. Rapid erosion of the spheres results in pores for cell seeding and vascularization with the matrix providing support until there is sufficient cell growth to create structural integrity.

U.S. Pat. No. 4,950,483 to Ksander et al. describes a collagen implant useful for wound healing. The implant is made of collagen and has a bulk density of 0.01 to 0.03 g/cm$^3$ and is said to have a pore size sufficient to permit cell ingrowth. Bioactive agents such as FGF and TGF-β may be incorporated into the implant.

U.S. Pat. No. 5,077,049 to Dunn et al. is directed to a method for restoring periodontal tissue. A biodegradable liquid polymeric systems designed to generate a porous structure when cured into a barrier membrane, is administered to the soft-tissue defect. The pores will form as a result of water-soluble material included in the liquid material. The liquid material injected into the defect provides a scaffold that is filled with new bone cells that gradually replace the water-soluble polymer.

U. S. Patent No. 4,902,295 to Walthall et al. involves a transplantable artificial tissue. The tissue is made by mixing a polymerizing matrix with reversible gel precursors in an aqueous solution with viable cells. The gel, which may be alginate, a gum or agarose, is then dissolved to provide a porous matrix for implantation.

None of the above-described references describes a biomedical implant material with a differentially degradable matrix and porosifying agent where polymerization occurs in situ or where the matrix is precast and is made of a biopolymeric material.

DISCLOSURE OF THE INVENTION

Accordingly, one aspect of the present invention is an in situ polymerizing biomedical implant useful for implantation into a patient comprising a slowly biodegradable matrix material and a biodegradable porosifying agent.

Another aspect of the invention is a precast biomedical implant useful for implantation into a patient comprising a slowly biodegradable polymeric matrix or a nonbiodegradable ceramic matrix and a biodegradable porosifying agent.

A further aspect of the invention is a method for repair of mammalian tissue using the above-described implants.

MODES OF CARRYING OUT THE INVENTION

Definitions

As used herein, certain terms will be used which have defined meanings.

By "biodegradable" or "bioerodible" as it relates to the porosifying agent is intended a material that will dissolve in situ as a result of exposure to an aqueous environment in less than a week, preferably about 1 and 72 hours, more preferably between about 2 and 12 hours. Dissolution may occur as a result of a number of different mechanisms such as simple diffusion, hydrolysis, enzymatic cleavage, ion exchange, autocatalysis, osmosis, degradation, free-radical cleavage, radiation effect, thermal melting, and chemical dissolution. Hydrolysis is the preferred mechanism for biodegradation. As such, the biodegradation of the porosifying material is distinguishable from prior art "leaching" of water-soluble drugs and salts, such as particulate calcium salts, e.g., tricalcium phosphate. Typically, these water-soluble drugs or salts merely create small voids or cavities on the surface of the matrix in contrast to the porous network provided by the biodegradable porosifying agents described herein.

By "slowly biodegradable" or "slowly bioerodible" as it relates to the matrix material is intended a material that will not dissolve in situ (or in an aqueous environment) within a week, or may dissolve in a period of from about one week to 24 months, preferably a period of between about 1 to 12 months. It also is intended to exclude material such as a polyether that is only degradable outside the range of normal body temperature and in organic solvents. Examples of this type of excluded polyether include low molecular weight aliphatic polyethers which are soluble in aqueous solutions of methanol, ethanol or acetone.

The term "porosifying agent" intends particulate materials that include but are not limited to materials in the form of solid or hollow spheres, extruded rods, or other convenient shapes. Typically, the particulate has a mean diameter of between about 10 and 500 μm, more typically between about 20 and 200 μm. The particles are generally spherical in shape but other shapes such as rhombic, irregular, stellate and other crystalline type shapes may be used. The agents are present in a concentration of at least about 12% per volume of the matrix material, preferably the concentration is between about 12 and 99% per volume of the matrix material, more preferably between about 20 and 90% per volume of the matrix material such that as the agent biodegrades a continuous porous network or pathway is formed within the implant. In one embodiment, components such as calcium salts, alginate, gum or agarose are specifically excluded.

The term "matrix" intends the portion of the implant material that acts as the support network; it is the slower biodegrading portion of the implant.

The term "continuous porous network" is intended to describe a network of micro-spacings or an internal micro-network formed by the biodegradation of the porosifying agent. The micropores are internally and externally interconnected to form a tunnel-like system or network within and throughout the matrix.

The Implant Material

This invention is to a biomedical implant comprising a non-toxic, slowly biodegradable biomedical matrix material and a non-toxic, biodegradable material that acts as a porosifying agent. The porosifying agent is present in sufficient quantity and particulate size to result in a continuous, porous network within the matrix once it has degraded.

The implant is biocompatible and is capable of solidifying when being cast or of solidifying and polymerizing in situ. Further, the matrix is slowly biodegradable as defined above and made from a material with a slower degradation rate than the porosifying agent. Degradation (or dissolution) rates of particular substances in water are generally available information.

Examples of matrix materials include but are not limited to collagen, fibrin, fibrinogen, polyorthoesters, polyvinyl alcohol, polyamides, polycarbonates, polyvinyl pyrrolidone, marine adhesive proteins, cyanoacrylates, analogs (e.g., fibrinogen analog as PCT WO 94/16085 to Irani for "Hybrid proteins having crosslinking and tissue binding activities", the contents incorporated herein by reference) mixtures, combinations and derivatives (e.g., methylated collagen, pegulated marine adhesives proteins) of the above. Preferred mixtures of the above for the matrix is a fibrin/collagen matrix in combination with gelatin as the porosifying agent. In one embodiment, polytetrafluoroethylene (PTFE), calcium phosphate ceramics, and materials that are not amenable to polymerization in situ such as polyethylene are specifically excluded as matrix materials.

The porosifying agent is biocompatible and biodegradable as described above. Examples of porosifying agents include but are not limited to gelatin, gelatinized collagen, collagen, fibrin, fibrinogen, proteins in solid state like albumin powder, degradable polyesters (polylactic or polyglycolic acid), polyethylene glycol (PEG), liposomes, lipids with emulsifiers, alginates, analogs, mixtures, combinations and derivatives of the above. Preferred mixtures of porosifying agents include pegulated particulates, albumin microspheres and gelatin. The porosifying agents may be in a solid state, such that they dissolve over a period of time or may they may be altered such that they are in a sparingly soluble state. This may be accomplished for example by altering the pI, for example by methylation or succinylation or by conjugating the porosifying agent to polyethylene glycol (MW 1 to 50 Kd) or by crosslinking said with glutaraldehyde.

In one embodiment, the matrix material is biodegradable but at a rate which is slower than the porosifying agent. Preferably, the matrix material is any of collagen, a collagen analog, e.g., gelatinized collagen, fibrinogen, or functional equivalents thereof. As such, materials such as PTFE and bone substitutes as described above are specifically excluded in that these materials are nonabsorbable yet biocompatible materials. Additionally, PTFE is not capable of polymerization in situ. When the matrix is composed of collagen, the collagen is preferably not chemically crosslinked, although it can be if desired.

In addition to the matrix material and porosifying agent, the implants may further include growth factors including but not limited to epidermal growth factor (EGF), transforming growth factor β (TGFβ-1, TGFβ-2), platelet derived growth factor (PDGF-AA, PDGF-AB, PDGF-BB), fibroblast growth factor (FGF), insulin-like growth factors (IGF), tumor necrosis factors (TNF), colony stimulating factors (CSFs), nerve growth factors (NGF), brain-derived neurotropic factor (BDNF (Amgen, Thousand Oaks, Calif. and Regeneron, Inc. Tarrytown, N.Y.), ciliary neurotropic factor (CNTF) (Amgen, Thousand Oaks, Calif. and Regeneron, Inc. Tarrytown, N.Y.) and the like, and/or therapeutic agents including but not limited to cytokines, interleukins (IL-1, IL-2) or other co-factors such as heparin or calmodulin, antibiotics, antineoplastic and antibacterials, to further stimulate or control tissue remodeling, or to control sepsis. These agents can be incorporated into the matrix material, the porosifying agent, or both. When the therapeutic is incorporated into the porosifying agent, it is released at rate greater than the matrix material.

An important characteristic of the implant is that the porosifying agent degrades faster than the matrix material. For example, if fibrin is used as the matrix, then polyethylene glycol or gelatin, which degrade more rapidly in water (and thus in situ) than does fibrin, may be used as the porosifying agent. However, if fibrin is used as the porosifying agent, then collagen may be used as the matrix since it degrades more slowly than does fibrin.

Preparation of the Implant
in situ Polymerizing Systems

In an in situ polymerization system, the porosifying agent may mixed as a dry phase with the matrix which may be in a semi-solid, liquid or dry particulate phase. An appropriate catalyst or co-factor may be added to the mixture or the porosifying agent itself may contain such catalyst or co-factor that will initiate polymerization.

Fibrin sealants are an example of an in situ polymerizing system. Fibrin sealants are two component tissue adhesive systems that are in a relatively viscous liquid form until both components are mixed together and polymerize at the surgical application site into a relatively dense gel. Thrombin in combination with $Ca^{2+}$ catalyzes the polymerization of fibrinogen, converting the fibrinogen into fibrin polymer. Further, thrombin and $Ca^{2+}$ activate coagulation Factor XIII, which effects covalent crosslinking of fibrin. The rate of proteolytic degradation of the fibrin polymer clot is decreased and mechanical stability is increased as a result of the covalent crosslinking of the polymer.

The fibrin polymer clot is porous, but only at a range of 1 to 5 micron in mean diameter, too small to permit cellular ingrowth. Accordingly, macrophage activity is sustained over periods of time longer than optimal for degradation and remodeling, and the fibrin polymer clot acts as a barrier until phagocytosis is complete. Where a porosifying agent is added according to the present invention, tissue reunion is improved as a result of the continuous pathway formed in the clot when the porosifying agent degrades in situ.

For systems where the matrix is made of fibrin, particulates may be incorporated directly into the fibrinogen component which is obtained in lyophilized form. The particulates may be alginate, gelatin, polyethylene glycol, polylactic acid/polyglycolic acid (PLA/PGA) hollow spheres, lipid in an emulsifier system (e.g., lecithin, Triton, lauryl sulfate, or Tween-80) hyaluronic acid and liposomes or other materials that degrade at a rate faster than the fibrin matrix and will create a continuous porous network once degraded. The porosifiers may be incorporated either in dry or liquid or semisolid form. Alternatively, the porosifier may be mixed just prior to, or during application of the system to the repair site. In another embodiment, collagen can be used as the matrix material of the inventive implants. When collagen is the matrix material, the porosifying agent may preferably contain an effective fibrin-forming amount of thromboplastin (Ortho Diagnostic, Raritan, N.J). These composites are particularly useful for tissue repair or effecting hemostasis by administering to the wound or treatment site a therapeutic amount of the composite. The particulate is preferably a hydrophilic porosifier such as gelatin, gelatinized collagen, fibrin, a salt or polyethylene glycol.

Pre-cast Systems

Alternatively, the matrix with the porosifying agent may be preformed and used for surgical reconstruction and drug delivery. In a particular embodiment, the implant is applied to the wound site as a dressing. The matrix material may be fibrin, alginate, collagen, PLA/PGA or other biocompatible polymers as well as rapidly dissolving ceramic based systems such as calcium sulfates, calcium phosphates, and the like. Porosifying agents such as gelatin, fibrin, polyethylene glycol are added to the matrix material. Exudate from the repair site anchors the dressing in place by infiltrating the porous network produced as a result of the degrading particulate. Tissue adhesives including but not limited to materials such as fibrin sealants and occlusive wraps and tapes may help to anchor the dressings in place.

Use of the Implant

When the implant is placed or applied to a desired site in vivo, the porosifying agent biodegrades relatively rapidly, thus leaving behind an inter-connecting network of pores to permit tissue and fluid influx into the matrix. The matrix then acts as a scaffolding for the migrating cells (e.g. macrophages, fibroblasts, and neovascular endothelial cells) and will degrade as these cells express connective tissue components for remodeling and regeneration.

The use of a matrix with a component that degrades in situ imparts several advantages over conventional porous implant configurations. First, porous implants tend to shrink in volume due to pressure from surrounding tissue, thus minimizing the benefits of controlled pore size and minimizing the amount of tissue ingrowth that can take place. Where a porosifying agent that degrades in situ is added, however, the cells involved in wound healing migrate into the network and minimize shrinkage of the implant.

A further benefit of an in situ degrading porosifying agent is that the porosifying agent acts as a mechanical stabilizer, permitting the formation of a porous network within the matrix. Materials such as gelatin, especially crosslinked gelatin, calcium alginate or fibrin are especially useful as the porosifying agent. Crosslinking may be accomplished by the addition of agents such as SPEG (polyethylene glycol succinimydyl), glutaraldehyde, diisocyonate, or dehydrothermally. Where calcium alginate is the porosifying agent, the guluronic/mannuronic acid segment ratio may be optimized for in vivo dissolution over the targeted period of time. Where fibrin is the porosifying agent, a high quantity of plasmin ($\geq 0.2$ mg/mL) is also useful, permitting a degradation rate proportional to the quantity of plasminogen present. Where polyethylene glycol particulate is used as the porosifying agent, a relatively rapid dissolution occurs (i.e. in less than 24 hours)

Another benefit derived from using an in situ biodegradable porosifying agent is that the mechanical properties of the implant both pre- and post-polymerization can be altered, tailoring the viscosity of the applied material and improving its mechanical stability in situ. The porosifying agent increases the stiffness modulus of the implant while it is still relatively undissolved. As dissolution occurs the contribution to the modulus by the porosifying agent decreases. Deposited ground substances (i.e. mucopolysaccharides, glycosaminoglycans, pectins and other proteoglycans) and collagen and inflammatory cells are exchanged, thus the overall modulus status remains roughly the same throughout the life-span of the matrix.

The rate of degradation of the implant materials will vary depending upon the material used (PEG the fastest, crosslinked gelatin the slowest) as well as the relative vascularity of the application site (liver, the fastest, subcutaneous, the slowest). A fibrin matrix will last usually from 5 to 14 days, depending upon concentration, plasminogen content and anatomic region. Higher fibrin and lower plasmin concentrations will decrease degradation rates. The addition of antiproteases such as ε-amino-n-caproic acid or aprotinin will retard degradation further. Once the implant is applied to the wound site, the porosifying agent begins to dissolve. This may occur in a matter of hours if the agent is polyethylene glycol or a matter of days if calcium alginate. The resultant porosity permits firm anchoring to the wound bed by host fibrin clots intercalating through the porous network. Leukocytes, macrophages, lymphocytes and fibroblasts then migrate through the pores, breaking down the fibrin implant matrix and initiating deposition of ground tissue substances (e.g. proteoglycans) and collagen. By way of example, implants tailored to last for 7 to 14 days may be applied to donor graft beds, chronic decubitus ulcers, resected tumor sites or bone tissue gaps.

In situ polymerizing systems are introduced into the repair site by a variety of means. They may be poured onto the site directly or by a dispenser which permits control of the amount of material in the system, as well as the area covered. The implants may be used as occlusive or fluid tight dressings or sealants in anatomic regions where it would be difficult to use a precast dressing, such as in endoscopic procedures. An example of a dispensing device is the DUPLOJECT® fibrin sealant delivery device (Immuno AG, Vienna, Austria).

Precast systems may be used as occlusive dressings. They are ultimately integrated into the repair site and facilitate tissue remodelling. In one embodiment, the precast systems contain an effective amount of thromboplastin as defined above. They may be suture, stapled, taped or wrapped into place. Generally, they are used as burn dressings or in tumor resection sites to facilitate reepitheliazation. Also, they may deliver growth factors or antimicrobials (e.g., gentamicin, penicillin, silver ions) or other metabolic modulators (e.g. calcitonin, interleukins).

It is apparent to those skilled in the art that the compositions described herein are useful for the preparation of medicaments for any suitable use, for example, tissue repair or for the release of therapeutic agents.

It is to be understood that while the invention has been described in conjunction with the preferred specific embodiments thereof, that the foregoing description as well as the examples that follow are intended to illustrate and not limit the scope of the invention. Other aspects, advantages and modifications within the scope of the invention will be apparent to those skilled in the biomedical implant art.

EXAMPLES

Example 1
Preparation of an in situ Polymerizing Fibrin Implant

In a tuberculin syringe with a 20 gauge needle, concentrated fibrinogen-Factor XIII (60 mg/mL) in tris-buffered saline (pH 7.2) is mixed with polyethylene glycol particulate (10000 MW, mean diameter 150 µm) to 50 vol %.

Example 2
Preparation of an in situ Polymerizing Calcium Alginate Implant

Calcium alginate microspheres (mean diameter 100 µm) prepared as described in Gospodarowicz and Cheng, *J. Cell Physiol* 128:475–484 (1986) which is herein incorporated by reference in its entirety. These are added in a syringe to 50 vol % as described in Example 1.

Example 3
Preparation of an in situ Polymerizing Gelatin Implant
SPEG-Crosslinked Gelatin 5 mL of concentrated collagen slurry in phosphate buffered saline (pH 7.2, 35 mg/mL, Zyderm I, Collagen Corp, Palo Alto, Calif.) is heated to 60° C. for 1 hour in a water bath, and then chilled to 37° C. to produce gelatin. Phosphate-buffered saline is added to dilute the gelatin concentration to 15 mg/mL. Sufficient SPEG is added to the gelatin solution for a final concentration of 10 mg/mL. The gelatin-SPEG solution is allowed to cool to room temperature and gel. The gel is lyophilized and pulverized by a grinding mill. The powder is sieved and particles in the range of 20 to 150 µm mean diameter are saved and sterilized by electron beam irradiation (2.5 Mrad dose).

The Matrix

The lyophilized SPEG crosslinked gelatin particulate is mixed with lyophilized fibrinogen-Factor XIII in a 1:1 v/v ratio. The powdered mixture is loaded into a dual plunger syringe system, containing both the lyophilate and the reconstituting buffer, Tris buffered saline (TBS). To reconstitute the gelatin-fibrinogen mixture, the plunger is depressed, forcing the diluent into the chamber containing the lyophilate. After several minutes incubation, the resultant slurry is ready to use.

Example 4
Preparation of a Pre-cast Fibrin Sealant System 12 vol % of polyethylene glycol particulate (MW 5 kd with a mean diameter of 20 to 100 µm) is mixed with the fibrinogen solution at a concentration of 30 mg/mL. The mixture is then poured into a mold. Polymerization of the fibrinogen is catalyzed by the addition of thrombin and $Ca^{2+}$, usually in a 1:1 v/v ratio. The catalyst is added rapidly and is thoroughly mixed to prevent settling of the particulate. 10 U/mL of thrombin is added for rapid polymerization. After gelling, the implant may be stored refrigerated (2–10° C.) or frozen (−20 to −150° ) until ready to use.

Example 5
Preparation of a Pre-cast Calcium Alainate System

Calcium alginate containing a minimum of 30% guluronic acid segments at 15 mg/mL in an aqueous solution is poured into a shallow rectangular mold. Gelatin is added as the porosifying agent at a concentration of 20 vol %. Concentrated calcium chloride solution is titrated rapidly into the alginate/gelatin mixture to a 0.1 M final concentration in the calcium alginate solution to effect gelling. Agitation of the mixture is necessary to minimize swelling of the particulate. The implant is sterilized by quick exposure to a liquid bactericide (e.g. alcohol) and stored at temperatures as described above.

Modifications of the above-described modes for carrying out the invention that are obvious to those of skill in the fields of chemistry, materials science, medicine and related fields are intended to be within the scope of the following claims.

I claim:

1. A method for forming a fibrin matrix at a tissue site comprising the steps of:

providing particulate crosslinked gelatin in dry, liquid or solid form;

mixing an effective fibrin-forming amount of thrombin with the particulate crosslinked gelatin to form a mixture; and allowing the mixture to further mix with fibrinogen at the tissue site.

* * * * *